United States Patent [19]
Alig et al.

[11] 4,197,406
[45] Apr. 8, 1980

[54] D-HOMOSTEROIDS

[75] Inventors: Leo Alig, Kaiseragust; Andor Fürst, Basel; Marcel Müller, Frenkendorf, all of Switzerland; Ulrich Kerb; Rudolf Wiechert, both of Berlin, Fed. Rep. of Germany

[73] Assignee: Hoffmann-La Roche Inc., Nutley, N.J.

[21] Appl. No.: 36,476

[22] Filed: May 7, 1979

[30] Foreign Application Priority Data

May 12, 1978 [CH] Switzerland .......................... 5207/78
Feb. 23, 1979 [CH] Switzerland .......................... 1841/79

[51] Int. Cl.$^2$ ..................... C07C 69/78; A61K 31/235
[52] U.S. Cl. ......................................... 560/6; 560/107; 424/305; 424/308
[58] Field of Search ..................................... 560/6, 107

[56] References Cited

U.S. PATENT DOCUMENTS

| 4,029,692 | 6/1977 | Alig | 560/6 |
| 4,033,995 | 7/1977 | Nickolson | 560/6 |

OTHER PUBLICATIONS

Breslow, J. Am. Chem. Soc., 93, p. 905 (1977).

*Primary Examiner*—Bernard Helfin
*Assistant Examiner*—Michael Shippin
*Attorney, Agent, or Firm*—Jon S. Saxe; George M. Gould; James H. Callwood

[57] ABSTRACT

The present disclosure is concerned with 17a-(m-iodobenzoyloxy) substituted D-homosteroids and a process for their manufacture. The compounds are useful as intermediates and also as hormonal agents, particularly progestational agents.

8 Claims, No Drawings

D-HOMOSTEROIDS

BACKGROUND OF THE INVENTION

Breslow et al., J.A.C.S. 99:3, 905 (1977) describe the preparation of a $\Delta^{9(11)}$ compound through the 9-chlorinated derivative of a compound of the formula

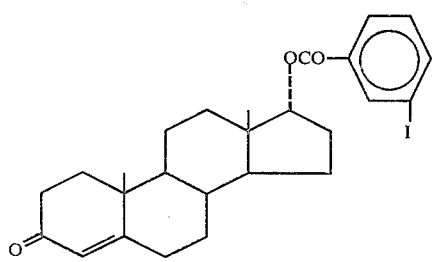

The D-homosteroids provided by the present invention have the following general formula

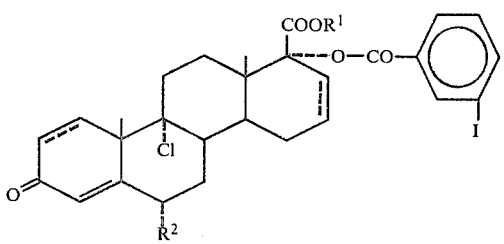

wherein the broken lines in the A- and D-rings denote optional bonds, $R^1$ represents a hydrogen atom or a lower alkyl group and $R^2$ represents a hydrogen or fluorine atom or a methyl group.

The term "lower alkyl" used herein means, in particular, alkyl groups which are the characterising groups of alkanols containing up to 4 carbon atoms; for example, methyl, ethyl, propyl, isopropyl, butyl and isobutyl. A preferred class of D-homosteroids of formula I comprises those in which the D-ring is saturated.

The D-homosteroids of formula I are primarily intermediates for the manufacture of pharmacologically valuable substances. However, they themselves also have pharmacological (e.g. hormonal) activity.

Examples of D-homosteroids of formula I are:

9α-Chloro-17a-(m-iodobenzoyloxy)-3-oxo-D-homoandrost-4-ene-17aβ-carboxylic acid, 9α-chloro-17a-(m-iodobenzoyloxy)-6α-methyl-3-oxo-D-homoandrost-4-ene-17aβ-carboxylic acid, 9α-chloro-6α-fluoro-17a-(m-iodobenzoyloxy)-3-oxo-D-homoandrost-4-ene-17aβ-carboxylic acid, 9α-chloro-17a-(m-iodobenzoyloxy)-3-oxo-D-homoandrosta-1,4-diene-17aβ-carboxylic acid, 9α-chloro-17a-(m-iodobenzoyloxy)-6α-methyl-3-oxo-D-homoandrosta-1,4-diene-17aβ-carboxylic acid, 9α-chloro-6α-fluoro-17a-(m-iodobenzoyloxy)-3-oxo-D-homoandrosta-1,4-diene-17aβ-carboxylic acid, 9α-chloro-17a-(m-iodobenzoyloxy)-3-oxo-D-homoandrosta-4,16-diene-17aβ-carboxylic acid, 9α-chloro-17a-(m-iodobenzoyloxy)-3-oxo-D-homoandrosta-1,4,16-triene-17aβ-carboxylic acid, 9α-chloro-6α-fluoro-17a-(m-iodobenzoyloxy)-3-oxo-D-homoandrosta-4,16-diene-17aβ-carboxylic acid, 9α-chloro-17a-(m-iodobenzoyloxy)-6α-methyl-3-oxo-D-homoandrosta-1,4,16-triene-17aβ-carboxylic acid, and the methyl, ethyl, propyl and butyl esters of these acids.

After cleaving the 9α-chlorine atom from the D-homosteroids of formula I there are obtained according to methods known per se, such as, for example, with silver perchlorate in the warm, with an alkali or alkaline earth metal carbonate in dimethylformamide or an organic base such as collidine, lutidine or pyridine or with an alkali hydroxide in an alcoholic solvent, the corresponding $\Delta^{9(11)}$-D-homosteroids. In the latter method ester groups which may be present are simultaneously also cleaved. The thus-obtained $\Delta^{9(11)}$-D-homosteroids are valuable starting materials for the manufacture of known 9α,11β-dihalo-D-homosteroids or 11β-hydroxy-D-homosteroids such as, for example, the D-homosteroids known from German Offenlegungsschrift No. 2,614,079.

The 9α,11β-dihalo-D-homosteroids are obtained, as is well-known, by adding bromine fluoride, chlorine fluoride or chlorine to a $\Delta^{9(11)}$-D-homosteroid. The 11β-hydroxy-9α-fluoro-D-homosteroids are obtained, as is well-known, by adding hypobromous acid to a corresponding $\Delta^{9(11)}$-D-homosteroid converting a resulting 11β-hydroxy-9α-bromo-D-homosteroid by hydrogen bromide cleavage into a 9β,11β-oxido-D-homosteroid and opening the epoxide ring with hydrogen fluoride. In order to obtain a 11β-hydroxy-D-homosteroid, a 11β-hydroxy-9α-bromo-D-homosteroid can also be debrominated with tributyltin hydride, Raney-nickel or chromium-(II) chloride.

The D-homosteroids of formula I have the particular advantage that they offer a ready access to the 11β-hydroxy-D-homosteroids which hitherto have been manufactured by microbiological hydroxylation. Whereas in microbiological methods costly provisions must be made (cultivation of the microorganisms, sterility of all fermentation media, large volumes), the 11β-hydroxy-D-homosteroids can be manufactured from the D-homosteroids of formula I by steps which are technically simple to realise.

The invention is also concerned with a process for the manufacture of the D-homosteroids of formula I, which process is characterised in that a D-homosteroid of the general formula

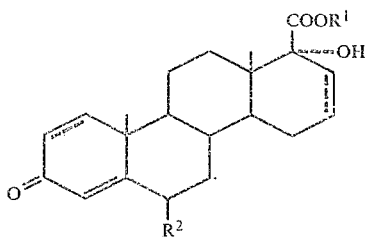

, wherein $R^1$, $R^2$ and the broken lines in the A- and D-rings have the significance given earlier, is esterified with a m-iodobenzoylating agent, if desired a free 17aβ-carboxy group is esterified, and the resulting 17aα-m-iodobenzoyl ester is treated with chlorine, sulphuryl chloride or iodobenzene dichloride and irradiated with long-wave UV-light or heated in the presence of a radical-former and, if desired, a free 17aβ-carboxy group is esterified.

From the work of Breslow et al. [e.g. J. Amer. Chem. Soc. 96 (1974) 1973, ibid. 96 (1974) 6791] it is known that, in the case of steroids which are esterified in the 3α-position, the tertiary carbon atom in the 9-position can be chlorinated with iodobenzene dichloride under the influence of light and subsequently hydrogen chloride can be cleaved off with the formation of a 9,11-double bond. However, this procedure has the disadvantage that it can only be used on such steroids which have no carboxy group or no unprotected carbonyl group in the 17β-side chain. According to the process provided by the present invention there are, however, selectively obtained 9α-chloro-3-oxo-D-homoandrost-4-ene-17aβ-carboxylic acids. It is also quite surprising that the chlorination takes place selectively in the 9-position, since from the work of Halpern [e.g. Chem. & Ind., 1962, 1571] it is known that steroids having double bonds react with iodobenzene dichloride to give the corresponding α-dichlorosteroids.

The process provided by the present invention is conveniently carried out by reacting a D-homosteroid starting material of formula II with a m-iodobenzoylating agent such as m-iodobenzoyl chloride or anhydride in the presence of an acid-binding agent (e.g. pyridine or triethylamine) or in the presence of a strong acid catalyst (e.g. p-toluenesulphonic acid). As the solvent for the m-iodobenzoylation there come into consideration organic solvents which do not contain hydroxyl groups (e.g. chlorinated hydrocarbons such as methylene chloride or hydrocarbons such as benzene). Thereby there is initially obtained a mixed anhydride of the steroid carboxylic acid and the m-iodobenzoic acid, which is cleaved by means of an acid (e.g. with aqueous hydrochloric acid) or by means of a base (e.g. with aqueous diethylamine) to give the desired 17aα-m-iodobenzoyloxy derivative of the D-homosteroid starting material of formula II.

The conversion of a thus-obtained 17aα-(m-iodobenzoyl)-D-homosteroid ester into a corresponding D-homosteroid of formula I is conveniently carried out in a suitable solvent. Suitable solvents are those which are not affected by the halogenating agent which is used, examples of such solvents being halogenated hydrocarbons such as methylene chloride, chloroform, carbon tetrachloride, trichloroethylene and dichloroethylene and aromatic hydrocarbons such as benzene, chlorobenzene and toluene. If desired, these solvents can also be used as mixtures with one another. Conveniently, the conversion is carried out with the exclusion of oxygen in a protective gas atmosphere. For this purpose, an inert gas such as nitrogen or argon is conducted into the solution. The irradiation with long-wave UV-light can be carried out using a commercially obtainable ultraviolet emitter (e.g. a mercury high-pressure lamp). As the radical-former there can be used an organic peroxide such as dibenzoyl peroxide, copper-(I) acetate or azodiisobutyronitrile. Conveniently, there are used 1 to 25, preferably 10, equivalents of the radical-former per 100 equivalents of the D-homosteroid to be chlorinated, in a solvent, for example one of the aforementioned halogenated hydrocarbons.

The esterification of a free 17aβ-carboxy group can be carried out according to methods known per se; for example, with a diazoalkane such as diazomethane in ether, or by reaction of a salt of the 17aβ-carboxylic acid (e.g. an alkali salt) with an alkyl halide such as methyl iodide.

The steroid starting materials of formula II, insofar as they are not known or are described hereinafter, can be prepared in analogy to known methods or methods described in the Examples.

The D-homosteroids of formula I have hormonal activity, especially on the endocrine system, and can accordingly be used as hormonally active agents (e.g. as progestational agents). They can be administered orally or parenterally at a daily dosage in the range of from about 0.005 mg/kg to 0.15 mg/kg.

The D-homosteroids of formula I can be used as medicaments; for example, in the form of pharmaceutical preparations which contain them in association with a compatible carrier material. The carrier material can be an organic or inorganic inert carrier material which is suitable for enteral, percutaneous or parenteral administration such as, for example, water, gelatin, gum arabic, lactose, starch, magnesium stearate, talc, vegetable oils, polyalkyleneglycols, petroleum jelly etc. The pharmaceutical preparations can be made up in solid form (e.g. as tablets, dragées, suppositories or capsules), in semi-solid form (e.g. as salves) or in liquid form (e.g. as solutions, suspensions or emulsions). The pharmaceutical preparations may be sterilised and/or may contain adjuvants such as preserving, stabilising, wetting or emulsifying agents, salts for varying the osmotic pressure or buffers. The pharmaceutical preparations can also contain other therapeutically valuable substances.

The following Examples illustrate the process provided by the present invention:

EXAMPLE 1

3.42 g of 17a-hydroxy-3-oxo-D-homoandrost-4-ene-17aβ-carboxylic acid [melting point 261° C.; $[\alpha]_D = +59°$ (methanol, c=0.1%); $\epsilon_{241} = 13,600$], obtained by oxidising 17a,21-dihydroxy-D-homo-pregn-4-ene-3,20-dione with periodic acid in aqueous methanol, are reacted for 2 hours at 0° C. with 4.1 ml of m-iodobenzoyl chloride in 98 ml of methylene chloride in the presence of triethylamine. Subsequently, the mixed anhydride obtained is converted by basic hydrolysis with aqueous diethylamine into 5 g of 17aα-(m-iodobenzoyloxy)-3-oxo-D-homoandrost-4-ene-17aβ-carboxylic acid of melting point 213°–214° C.; $[\alpha]_D = -33°$ (dioxan, c=0.1%); $\epsilon_{220} = 32,400$.

218 mg of 17a-(m-iodobenzoyloxy)-3-oxo-D-homoandrost-4-ene-17aβ-carboxylic acid and 104 mg of iodobenzene dichloride were gasified with argon in 22 ml of chloroform for 5 minutes and subsequently irradiated with a mercury high-pressure lamp for 30 minutes. The chloroform solution was washed with sodium bisulphite solution and dilute sodium chloride solution, dried and evaporated. From methylene chloride there was obtained crystalline 9α-chloro-17a-(m-iodobenzoyloxy)-3-oxo-D-homoandros-4-ene-17aβ-carboxylic acid which melted at 232°–233° C. after recrystallisation from acetone/hexane; $[\alpha]_D = -58°$ (dioxan, c=0.1%); $\epsilon_{220} = 33,800$.

288 mg of 17a-(m-iodobenzoyloxy)-3-oxo-D-homoandrost-4-ene-17aβ-carboxylic acid, 151 mg of iodobenzene dichloride and 12.1 mg of dibenzoyl peroxide were boiled at reflux under argon in 50 ml of carbon tetrachloride for 1.25 hours. The mixture was diluted with chloroform, washed with sodium bisulphite solution and dilute sodium chloride solution, dried and evaporated. Chromatography of the residue on silica gel with ether containing 1% acetic acid gave 9α-chloro-17a-(m-iodobenzoyloxy)-3-oxo-D-homoandrost- 4-ene-17aβ-carboxylic acid of melting point 232°–233° C. (from acetone/hexane). Chloroform can be used in place of carbon tetrachloride in this procedure.

740 mg of 9α-chloro-17a-(m-iodobenzoyloxy)-3-oxo-D-homoandrost-4-ene-17aβ-carboxylic acid in 50 ml of acetone were treated with 400 mg of silver perchlorate in 14 ml of water. The mixture was boiled at reflux under argon for 5 hours. The mixture was treated with 1 ml of saturated sodium chloride solution, filtered and concentrated in vacuo. The residue was washed twice in methylene chloride with dilute sodium chloride solution and the methylene chloride solution was dried and evaporated. Chromatography on silica gel with ether containing 1% acetic acid gave pure 17a-(m-iodobenzoyloxy)-3-oxo-D-homoandrosta-4,9(11)-diene-17aβ-carboxylic acid of melting point 238°–239° C. (from acetone/hexane); $[\alpha]_D = -38°$ (dioxan, c=0.1%); $\epsilon_{220} = 35,100$.

130 mg of 17a-(m-iodobenzoyloxy)-3-oxo-D-homoandrosta-4,9(11)-diene-17aβ-carboxylic acid and 860 mg of potassium hydroxide pellets were stirred at 95° C. in 4.5 ml of ethyleneglycol under argon for 24 hours. After the addition of 1 ml of acetic acid, the mixture was poured into dilute hydrochloric acid and extracted three times with methylene chloride. The organic phases were washed neutral with water and dilute sodium chloride solution, dried and evaporated in vacuo. Chromatography of the residue on silica gel gave 17a-hydroxy-3-oxo-D-homoandrosta-4,9(11)-diene-17aβ-carboxylic acid of melting point 255°–256° C. (from acetone); $[\alpha]_{365} = -296°$ (dioxan, c=0.1%); $\epsilon_{240} = 17,400$.

140 mg of 9α-chloro-17a-(m-iodobenzoyloxy)-3-oxo-D-homoandrost-4-ene-17aβ-carboxylic acid and 920 mg of potassium hydroxide pellets were stirred at 95° C. in 5 ml of ethyleneglycol for 20 hours under argon. After the addition of 1 ml of acetic acid, there was obtained as described earlier 17a-hydroxy-3-oxo-D-homoandrosta-4,9(11)-diene-17aβ-carboxylic acid.

EXAMPLE 2

1 g of 17a-(m-iodobenzoyloxy)-3-oxo-D-homoandrost-4-ene-17aβ-carboxylic acid, 1 g of sodium hydrogen carbonate, 1 ml of methyl iodide and 7.5 ml of dimethylacetamide were stirred at 25° C. for 20 hours. The mixture was worked-up with ether and dilute hydrochloric acid to give 17a-(m-iodobenzoyloxy)-3-oxo-D-homoandrost-4-ene-17aβ-carboxylic acid methyl ester as a non-crystalline foam; $[\alpha]_D = -32°$ (dioxan, c=0.1%); $\epsilon_{221} = 34,500$.

600 mg of 17a-(m-iodobenzoyloxy)-3-oxo-D-homoandrost-4-ene-17aβ-carboxylic acid methyl ester and 350 mg of iodobenzene dichloride were dissolved in 20 ml of distilled methylene chloride. After passing argon through the solution for 5 minutes, the solution was irradiated with a mercury high-pressure lamp for 10 minutes. The solution was washed with aqueous sodium bisulphite solution and dilute sodium chloride solution, dried and evaporated. Chromatography of the residue on silica gel with ether/hexane gave 9α-chloro-17a-(m-iodobenzoyloxy)-3-oxo-D-homoandrost-4-ene-17aβ-carboxylic acid methyl ester of melting point 224°–225° C. (from acetone/hexane); $\epsilon_{222} = 35,400$; $[\alpha]_D = -51°$ (dioxan, c=0.1%).

In a manner analogous to that described in Example 1, from 9α-chloro-17a-(m-iodobenzoyloxy)-3-oxo-D-homoandrost-4-ene-17aβ-carboxylic acid methyl ester there was obtained, via 17a-(m-iodobenzoyloxy)-3-oxo-D-homoandrosta-4,9(11)-diene-17aβ-carboxylic acid methyl ester $[\epsilon_{221} = 36,000; [\alpha]_D = -28°$ (dioxan, c=0.1%)], 17a-hydroxy-3-oxo-D-homoandrosta-4,9(11)-diene-17aβ-carboxylic acid of melting point 255°–256° C.

EXAMPLE 3

By treating 17a-hydroxy-3-oxo-D-homoandrosta-1,4-diene-17aβ-carboxylic acid with m-iodobenzoyl chloride in methylene chloride in the presence of triethylamine and subsequent basic hydrolysis of the resulting mixed anhydride there was obtained 17a-(m-iodobenzoyloxy)-3-oxo-D-homoandrosta-1,4-diene-17aβ-carboxylic acid of melting point 210°–211° C.; $\epsilon_{220} = 32,800$; $[\alpha]_D = -40°$ (dioxan, c=0.1%).

700 mg of 17a-(m-iodobenzoyloxy)-3-oxo-D-homoandrosta-1,4-diene-17aβ-carboxylic acid and 369 mg of iodobenzene dichloride in 140 ml of chloroform were flushed with argon for 5 minutes and subsequently irradiated for 25 minutes with a mercury high-pressure lamp. The chloroform solution was washed with sodium bisulphite solution and sodium chloride solution, dried and evaporated in vacuo. From acetone/hexane there was obtained crystalline 9α-chloro-17a-(m-iodobenzoyloxy)-3-oxo-D-homoandrosta-1,4-diene-17aβ-carboxylic acid of melting point 252°–253° C.; $[\alpha]_D = -28°$ (dioxan, c=0.1%); $\epsilon_{220} = 34,600$.

In a manner analogous to that described in Example 1, from 9α-chloro-17a-(m-iodobenzoyloxy)-3-oxo-D-homoandrosta-1,4-diene-17aβ-carboxylic acid there was obtained, via 17a-(m-iodobenzoyloxy)-3-oxo-D-homoandrosta-1,4,9(11)-triene-17aβ-carboxylic acid [melting point 228°–229° C.; $[\alpha]_D = -90°$ (dioxan, c=0.1%); $\epsilon_{219} = 35,000$], 17a-hydroxy-3-oxo-D-homoandrosta-1,4,9(11)-triene-17aβ-carboxylic acid of melting point 267°–268° C. (from acetone/hexane); $[\alpha]_D = -95°$ (dioxan, c=0.1%); $\epsilon_{239} = 15,500$.

The starting material can be prepared as follows:

21-Acetoxy-17a-hydroxy-D-homopregn-4-ene-3,20-dione is dehydrogenated with selenium dioxide in tert.-butanol to give 21-acetoxy-17a-hydroxy-D-homopregna-1,4-diene-3,20-dione [melting point 220°–221° C.; $[\alpha]_D = +102°$ (dioxan, c=0.1%); $\epsilon_{244} = 15,700$], this is converted with potassium carbonate in aqueous methanol into 17a,21-dihydroxy-D-homopregna-1,4-diene-3,20-dione [melting point 236°–237° C.; $[\alpha]_D = +76°$ (dioxan, c=0.1%); $\epsilon_{244} = 12,400$] and the latter is degraded with periodic acid in methanol/water to give 17a-hydroxy-3-oxo-D-homoandrosta-1,4-diene-17aβ-carboxylic acid of melting point 226°–227° C.; $[\alpha]_D = +24°$ (dioxan, c=0.1%); $\epsilon_{246} = 14,900$.

EXAMPLE 4

In a manner analogous to that described in Example 1, from 6α-fluoro-17a-hydroxy-3-oxo-D-homoandrost-4-ene-17aβ-carboxylic acid there is obtained, via 6α-fluoro-17aα-(m-iodobenzoyloxy)-3-oxo-D-homoandrost-4-ene-17aβ-carboxylic acid [melting point 216°–217° C., $[\alpha]_D = -30°$ (dioxan, c=0.1%); $\epsilon_{221} = 35,770$], 9α-chloro-6α-fluoro-17a-(m-iodobenzoyloxy)-3-oxo-D-homoandrost-4-ene-17aβ-carboxylic acid of melting point 222°–224° C.; $[\alpha]_D = -54°$ (dioxan, c=0.1%); $\epsilon_{220} = 31,880$.

EXAMPLE 5

In a manner analogous to that described in Examples 1–3, from 17a-hydroxy-3-oxo-D-homoandrosta-4,16-diene-17aβ-carboxylic acid there is obtained, via 17a-

(m-iodobenzoyloxy)-3-oxo-D-homoandrosta-4,16-diene-17aβ-carboxylic acid methyl ester [melting point 171°–172° C.; $[\alpha]_D = 152°$ (dioxan, c=0.1%); $\epsilon_{221} = 35,810$], 9α-chloro-17a-(m-iodobenzoyloxy)-3-oxo-D-homoandrosta-4,16-diene-17aβ-carboxylic acid methyl ester of melting point 208° C.; $[\alpha]_D = -134°$ (dioxan, c=0.1%); $\epsilon_{221} = 36,750$.

The following Example illustrates a pharmaceutical preparation containing the D-homosteroids provided by the present invention:

EXAMPLE A

Tablets of the following composition are produced in a manner known per se:

| | | |
|---|---|---|
| Active ingredient, e.g. 9α-chloro-17a-(m-iodobenzoyloxy)-3-oxo-D-homoandrost-4-ene-17aβ-carboxylic acid methyl ester | 1 | mg |
| Lactose | 60 | mg |
| Starch | 37 | mg |
| Talc | 1.8 | mg |
| Magnesium stearate | 0.2 | mg |
| | 100.0 | mg |

We claim:

1. A D-homosteroid of the formula

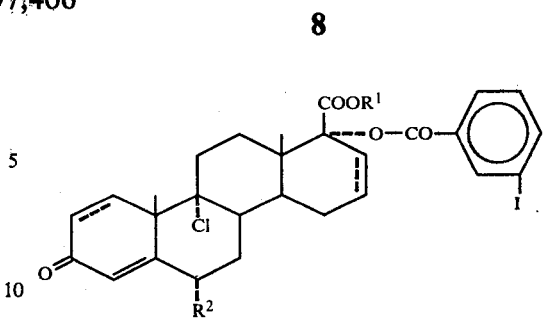

wherein the broken lines in the A- and D-rings denote optional bonds, $R^1$ is hydrogen or lower alkyl and $R^2$ is hydrogen, fluorine or methyl.

2. The D-homosteroid of claim 1 which is 9α-chloro-17a(m-iodobenzoyloxy)-3-oxo-D-homoandrosta-4,16-diene-17aβ-carboxylic acid methyl ester.

3. The D-homosteroid of claim 1 in which the D-ring is saturated.

4. The D-homosteroid of claim 3 which is 9α-chloro-17a-(m-iodobenzoyloxy)-3-oxo-D-homoandrosta-1,4-diene-17aβ-carboxylic acid.

5. The D-homosteroid of claim 3 in which the D-ring is saturated and the A-ring is mono-unsaturated.

6. The D-homosteroid of claim 5 which is 9α-chloro-17a-(m-iodobenzoyloxy)-3-oxo-D-homoandrost-4-ene-17aβ-carboxylic acid.

7. The D-homosteroid of claim 5 which is 9α-chloro-17a-(m-iodobenzoyloxy)-3-oxo-D-homoandrost-4-ene-17aβ-carboxylic acid methyl ester.

8. The D-homosteroid of claim 5 which is 9α-chloro-6α-fluoro-17a-(m-iodobenzoyloxy)-3-oxo-D-homoandrost-4-ene-17aβ-carboxylic acid.

* * * * *